United States Patent [19]

Adair

[11] 4,184,496
[45] Jan. 22, 1980

[54] AIR MOVING SIMULATED CIGARETTE DEVICE

[76] Inventor: Virginia M. Adair, 1080 W. Paces Ferry Rd., NW., Atlanta, Ga. 30327

[21] Appl. No.: 880,622

[22] Filed: Feb. 23, 1978

[51] Int. Cl.² .................. A24D 47/00; A61M 15/06; A63J 3/00; A63J 5/00
[52] U.S. Cl. ........................................ 131/170 A
[58] Field of Search ........... 131/171 R, 171 A, 170 R, 131/170 A, 198 R, 198 A, 200, 209, 215 R, 215 A, 216, 178; 128/208; 46/9; 272/8 R, 8 N

[56] References Cited

U.S. PATENT DOCUMENTS

| | | | |
|---|---|---|---|
| 2,797,691 | 7/1957 | Butler | 131/178 X |
| 2,996,006 | 8/1961 | Marquette | 131/171 A |
| 3,200,819 | 8/1965 | Gilbert | 131/171 AM X |
| 3,404,692 | 10/1968 | Lampert | 131/170 A |
| 3,410,273 | 11/1968 | Bolles | 131/171 A |
| 3,565,071 | 2/1971 | Cobb et al. | 131/198 R X |
| 3,695,275 | 10/1972 | Hayword | 131/171 A |
| 4,083,372 | 4/1978 | Boden | 131/170 A X |

FOREIGN PATENT DOCUMENTS 2430658  1/1976  Fed. Rep. of Germany ...... 131/170 A

Primary Examiner—Vincent Millin
Attorney, Agent, or Firm—Cushman, Darby & Cushman

[57] ABSTRACT

A device for enabling a user while simulating the action of smoking a cigarette or cigar to circulate the air surrounding his nose and mouth which may be laden with actual cigarette or cigar smoke of others in the vicinity. The device comprises a mouthpiece member having an exterior simulating a cigarette holder and a tubular member having an exterior simulating the exterior of a cigarette. The mouthpiece and tubular member have a continuous passage extending from the mouth engaging end of the mouthpiece to the free end of the tubular member through which a substantial flow of air can be established by the user blowing into the end of the mouthpiece so that a substantial current of air flows outwardly from the end of the tubular member. The mouthpiece has air aspirating openings extending from the exterior thereof into aspirating relation with the main passage so that when a substantial flow of air is established within the passage as aforesaid, the flow will aspirate additional air through the air aspirating openings.

6 Claims, 3 Drawing Figures

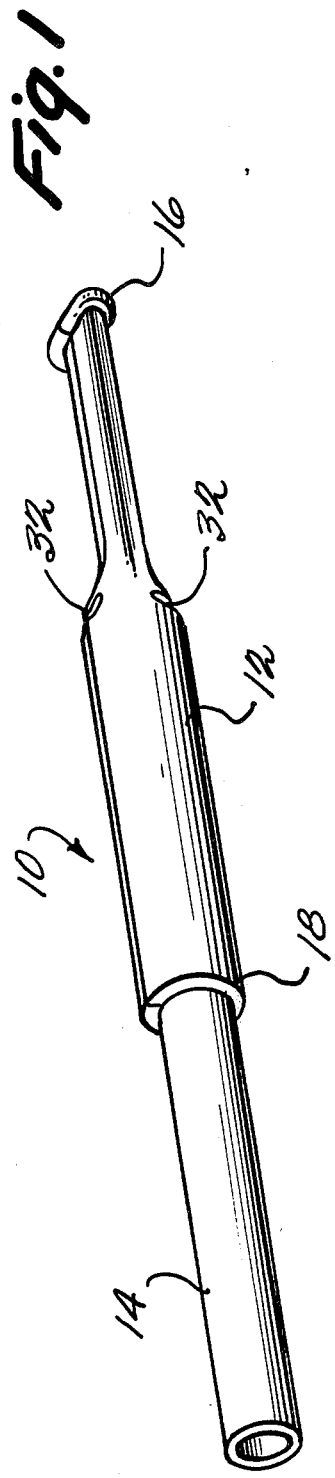
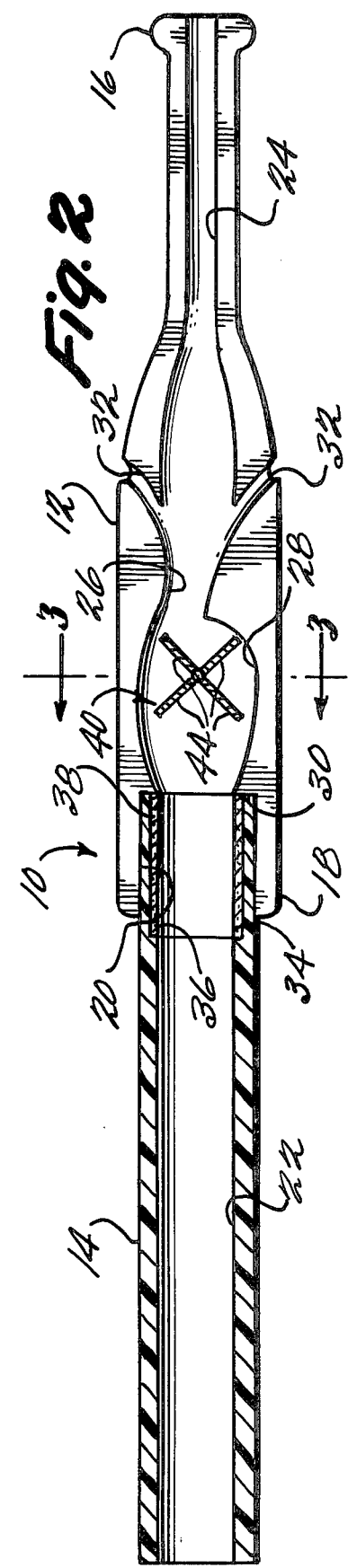
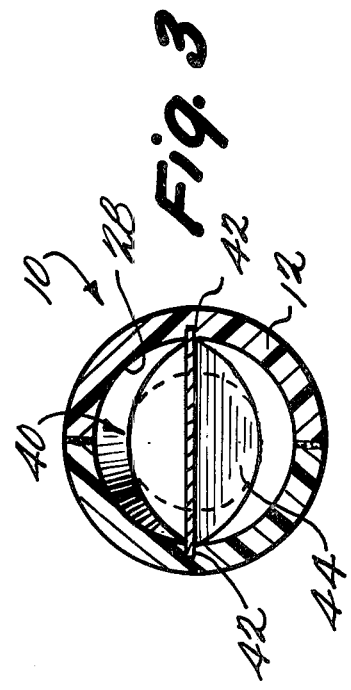

AIR MOVING SIMULATED CIGARETTE DEVICE

This invention relates to air purification, and more particularly to a device which can be used to disperse tobacco smoke within close proximity to the nose and mouth of the user.

In recent years the health hazards associated with tobacco smoking have resulted in a great number of individuals giving up the habit. Indeed, it is often the case, particularly with those who have quit smoking, to find the smell of tobacco smoke in the air particularly distasteful. While there have been many devices proposed for enabling a smoker to gradually give up the smoking habit, there is nothing available to the individual who has given up smoking which would provide a substitute for the manual and oral manipulation of a cigarette and at the same time provide the user with the ability to disperse cigarette smoke imparted into the air by others in the vicinity of the user's mouth and nose.

It is an object of the present invention to provide a device which will fulfill the above-mentioned need. In accordance with the principles of the present invention, this objective is obtained by providing a mouthpiece member having an exterior simulating a cigarette or cigar holder and a tubular member having an exterior simulating the exterior of a cigarette or cigar engaged within the end of the mouthpiece member opposite from the mouth engaging end thereof. The mouthpiece and tubular member have a continuous passage extending therethrough of a size enabling the user to establish a substantial flow of air through the passage by blowing into the mouth end of the mouthpiece. The passage is substantially unobstructed so that a current of air flows outwardly from the tubular member with sufficient force to disperse the smoke in the immediate vicinity. In addition, the mouthpiece has formed therein air aspirating passage means extending from the exterior thereof into aspirating relation with the main passage so that when the aforesaid substantial flow of air is established within the main passage the flow will aspirate additional air through the air aspirating passage means. In this way, smoke within the air in the vicinity of the user's mouth and nose is dispersed through the air aspirating passages while the user is manually and orally manipulating the device in the manner of a cigarette or cigar in a holder.

Preferably, an air freshener cartridge is mounted within the main interior passage so as to disperse an air freshener into the flow established through the main passage. A further optional feature involves the provision of a rotatable impeller within the main passage to which motion is imparted by virtue of the user blowing into the mouthpiece, the inertia of the rotary impeller serving to continue the flow and aspiration of air through the passage for a short time after the user has stopped blowing, thus enabling the user to disperse smoke after he has removed the device from his mouth.

These and other objects of the present invention will become more apparent during the course of the following detailed description and appended claims.

The invention may best be understood with reference to the accompanying drawings, wherein an illustrative embodiment is shown.

In the drawings:

FIG. 1 is a perspective view of a device embodying the principles of the present invention;

FIG. 2 is a longitudinal sectional view of the device shown in FIG. 1; and

FIG. 3 is an enlarged sectional view taken along the line 3—3 of FIG. 2.

Referring now more particularly to the drawings, there is shown therein a device, generally indicated at 10, which embodies the principles of the present invention. In its broadest form, the invention includes a mouthpiece member 12 having an exterior simulating a cigarette holder and a tubular member 14 having an exterior simulating the exterior of a cigarette. It will be understood that the mouthpiece member may have an exterior simulating a cigar holder and the tubular member may have an exterior simulating a cigar.

The mouthpiece member has one end, indicated at 16, shaped to be engaged by the mouth of the user and an opposite end, indicated by the numeral 18, shaped to receive one end of the tubular member. Preferably, the mouthpiece member is molded of a plastic material, as for example, polypropylene, into two halves which are fixedly secured together as by cement or the like. The tubular member 14 is formed of a softer plastic material, as for example, polyethylene, and has one end adapted to be press fit within a counterbore 20 formed on the interior periphery of the end 18 of the mouthpiece member 12. It will be noted that the tubular member 14 is of relatively thin well construction providing an interior passage 22 of relatively large cross-sectional configuration. Similarly, the mouthpiece member 12 is formed with an interior passage 24 which extends from the mouth engaging end 16 to the tubular member receiving end 18 thereof. The passage 24 is also of substantial cross-sectional area and includes a central throat portion 26 which leads to the upper portion of a spherical impeller chamber 28. The spherical chamber 28 leads to the counterbore 20, there being a shoulder 30 formed at the inner end of the counterbore which is engaged by the associated end of the tubular member 14.

It will be understood that the device 10 of the present invention is useful in the form already described wherein the mouthpiece member and tubular member 14 provide a relatively large passage through which a user can establish a flow by blowing into the end 16 of the mouthpiece member 12 so that a substantial current of air will issue from the free end of the tubular member 14. In accordance with the principles of the present invention, formed in the central portion of the wall of the mouthpiece member 12 is a plurality of air aspirating openings or passages 32 which extend from the exterior of the mouthpiece member 12 into aspirating relation with the main passage 24. As shown, the air aspirating openings 32 communicate with the main passage at a position just rearwardly of the throat 26.

It is preferable in accordance with the principles of the present invention to provide a means within the device for freshening the air during the operation of the device. To this end, the interior periphery of the tubular member 14 is formed with a counterbore 34 in the end thereof which engages within the end 18 of the mouthpiece member 12. Mounted within the counterbore 34 between a shoulder 36 formed therein within the tubular member 14 and the shoulder 30 of the mouthpiece member when the tubular member is mounted therein is a cylindrical cartridge 38 formed of porous cellulose material impregnated with an air freshener. It will be noted that the interior diameter of the cylindrical cartridge 38 is generally equal to the interior diameter of the passage 22 so as not to provide an obstruction to the free flow of air through the device from the mouth engaging end 16 thereof outwardly of the free end of the tubular member 14.

With reference to FIG. 3, there is shown therein an optional impeller feature of the present invention which preferably is provided although it will be understood that it is within the contemplation of the present invention to provide a device which does not include the impeller feature. As shown, the spherical chamber 28 within the mouthpiece member 12 has a rotary impeller 40 mounted therein which includes a pair of stub shafts 42 and a plurality of radially extending blades 44 of generally semi-circular cross-sectional configuration.

Since the mouthpiece member 12 and tubular member 14 of the device 10 simulate the exterior configuration of a cigarette holder and a cigarette, the device 10 can be digitally and orally handled in exactly the same manner as a real cigarette in a real holder. When the user encounters a situation in which others in the vicinity are emitting tobacco smoke into the air, the user places the end 16 of the mouthpiece member 12 in his mouth and by blowing through the passage within the mouthpiece member establishes a flow of air through the passage 24, throat 26, chamber 28 and through the passage 22 of the member 14, so that it issues from the free end of the member 14 with a substantial current. The current of air issuing from the end of the tubular member tends to cause the air in the vicinity of the user's nose and mouth to move in a direction away from the device 10. At the same time, the flow of air through the passage 24 and throat 26 serves to aspirate air adjacent the mouth and nose of the user through the air aspirating openings 32. This movement of the air further tends to disperse any smoke therein which is adjacent to the mouth and nose of the user.

It will be understood that where the air freshener cartridge 38 is provided, the device will serve to not only circulate the air in the vicinity of the nose and mouth of the user but to impart an air freshener to the air as well, by virtue of the flow through the device 10 past the air freshener cartridge 38. It will also be understood that after an air freshener cartridge has been used for a time, it can be replaced with a new cartridge by simply removing the tubular member 14 from the mouthpiece member 12, replacing the used cartridge with a new one, and then replacing the tubular member 14 within the mouthpiece member 12.

Where the impeller 40 is provided, it will be noted that flow of air through the device will serve to effect a rotational movement of the impeller, which movement will continue by virtue of the inertial forces involved to rotate after the user has ceased blowing through the end 16 of the mouthpiece member 12. In this way air flow can be maintained for a short period after the user has removed the device 10 from his mouth.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. A device for enabling a user while simulating the action of smoking a cigarette or cigar, to circulate the air surrounding his nose and mouth which may be laden with actual cigarette or cigar smoke of others in the vicinity, said device comprising:

a tubular member having an exterior simulating the exterior of a cigarette or cigar extending from one end thereof to an opposite end thereof, a mouthpiece member having an exterior simulating a cigarette or cigar holder, said mouthpiece member having one end shaped to be engaged within the mouth of a user and an opposite end connected with said one end of said tubular member, said mouthpiece and said tubular member having a continuous passage extending from said one end of said mouthpiece to said opposite end of said tubular member through which a substantial flow of air can be established by the user blowing into said one end of said mouthpiece so that a substantial current of air flows outwardly from said opposite end of said tubular member, said mouthpiece having air aspirating passage means extending from the exterior thereof into aspirating relation with said passage so that when a substantial flow of air is established within said passage as aforesaid, said flow will aspirate additional air through said air aspirating passage means.

2. A device as defined in claim 1 including a fan rotor operatively disposed within said passage for rotary movement in response to the establishment of a flow of air within said passage as aforesaid so that said fan rotor will continue by inertia to rotate for a short period after the user stops blowing into said mouthpiece member.

3. A device as defined in claim 2 wherein said mouthpiece member includes a generally spherically shaped fan rotor receiving cavity communicating with said passage along one hemispherical portion thereof, said fan rotor being rotatably mounted in said mouthpiece member for rotational movement about an axis coincident with an axis of said spherically shaped cavity and transverse to the longitudinal extent of said passage, said fan rotor including a plurality of fan blades spaced annularly about said axis of rotation and shaped so that the free edges thereof move in a rotational path closely adjacent the periphery of said spherically shaped cavity.

4. A device as defined in claim 1, 2 or 3 including a member containing an air freshener removably mounted within said passage for imparting said air freshener to the established flow of air through said passage.

5. A device as defined in claim 4 wherein said tubular member is removably threadedly engaged within the opposite end of said mouthpiece member.

6. A device as defined in claim 5 wherein said one end of said tubular member is formed with an interior recess, said cartridge being removably disposed within said recess and being of cylindrical shape having a cylindrical interior passage extending therethrough defining a portion of said passage.

* * * * *